United States Patent
Yoshida et al.

(10) Patent No.: US 8,027,819 B2
(45) Date of Patent: Sep. 27, 2011

(54) FRACTURE PREDICTION DEVICE FOR SPOT WELDED PORTION, METHOD OF THE SAME, SOFTWARE ARRANGEMENT, AND COMPUTER-ACCESSIBLE MEDIUM

(75) Inventors: Hiroshi Yoshida, Chiba (JP); Naruhiko Nomura, Chiba (JP); Akihiro Uenishi, Chiba (JP)

(73) Assignee: Nippon Steel Corporation, Tokyo (JP)

( * ) Notice: Subject to any disclaimer, the term of this patent is extended or adjusted under 35 U.S.C. 154(b) by 865 days.

(21) Appl. No.: 10/599,921

(22) PCT Filed: Apr. 12, 2005

(86) PCT No.: PCT/JP2005/007100
§ 371 (c)(1),
(2), (4) Date: Oct. 13, 2006

(87) PCT Pub. No.: WO2005/100949
PCT Pub. Date: Oct. 27, 2005

(65) Prior Publication Data
US 2007/0199924 A1    Aug. 30, 2007

(30) Foreign Application Priority Data

Apr. 13, 2004 (JP) .................................. 2004-118201
Apr. 8, 2005 (JP) .................................. 2005-112644

(51) Int. Cl.
*G06F 17/50* (2006.01)
*G06G 7/48* (2006.01)
*B23K 9/10* (2006.01)

(52) U.S. Cl. .................................. 703/7; 703/1; 219/109

(58) Field of Classification Search .................. 703/1, 7; 219/109
See application file for complete search history.

(56) References Cited

U.S. PATENT DOCUMENTS
7,505,885 B2 *    3/2009    Deobald et al. .................... 703/7

FOREIGN PATENT DOCUMENTS
JP            06182561           7/1994
(Continued)

OTHER PUBLICATIONS

"Ultimate Strength and Failure Mechanism of Resistance Spot Weld Subjected to Tensile, Shear, or Combined Tensile/Shear Loads". Yuh J. Chao. Apr. 2003.*

(Continued)

*Primary Examiner* — Paul Rodriguez
*Assistant Examiner* — Nithya Janakiraman
(74) *Attorney, Agent, or Firm* — Dorsey & Whitney LLP (57) ABSTRACT

According to exemplary embodiments of the present invention, a fracture prediction device for a spot welded portion can be provided. For example, the device may include an input arrangement configured to input all or some of a material strength, a plate thickness, a nugget diameter of a spot welding, a plate width of a joint, and a rotation angle of the joint in a tension test, based on a cross tension test and/or a shear tension test at a spot welded joint. The device can also include a first calculation arrangement configured to calculate a fracture strength parameter of the spot welded portion. A parameter storage arrangement may also be provided which can be configured to store the fracture strength parameter by each steel type. Further, the device may further have a second calculation arrangement configured to determine a fracture of the spot welded portion.

28 Claims, 9 Drawing Sheets

FOREIGN PATENT DOCUMENTS

| | | |
|---|---|---|
| JP | 2002031627 | 1/2002 |
| JP | 2002316267 | 10/2002 |
| RU | 2 133 179 | 7/1999 |
| WO | WO02/071162 A1 | 12/2002 |

OTHER PUBLICATIONS

"Large cold plastic deformation of metal-matrix composites reinforced by SiC particles". Jian Jiang. 1993.*

"The role of the interfacial strength in glass bead filled HDPE" Shu-Lin Bai, et al. Journal of Materials Science Letters 19, 2000, 1587-1589.*

Office Action of Russian Patent Application No. 2006139948.

Miyuki Yamamoto et al. "Characteristics comparison of some welding methods for sheet material and crashworthiness performance of model member", No. 9705 JSAE Symposium, Mar. 25, 1997, pp. 39-44.

"Specimen dimensions and procedure for shear testing resistance spot and embossed projected welded joints", Japanese Industrial Standard, Mar. 20, 1999, pp. 1-10.

"Specimen dimensions and procedure for cross tension testing resistance spot and embossed projected welded joints", Japanese Industrial Standard, Mar. 20, 1999, pp. 1-8.

Office Action of associated Russian Patent Application No. 2006139948 with English-language translation thereof.

International Preliminary Report of Patentability and Written Opinion for International Application No. PCT/JP2005/007100.

Osamu Takatori et al., "Crash Simulation on Rail Car Body", JARI Research Journal vol. 24, No. 7, Jul. 1, 2002, pp. 265-268.

Eizaburo Nakanishi et al., "Possibilities of Prediction of Failure at Spot Welds in a Car Collision", Society of Automotive Engineering of Japan, No. 88-00, Oct. 17, 2000, pp. 1-4.

Teruaki Inoue et al., "A Crash Simulation Analysis which Consider The Spot Weld Rupture", Society of Automotive Engineering of Japan, No. 88-00, Oct. 17, 2000, pp. 5-7.

The Comprehensive Soviet Encyclopedia. (1976) pp. 27-28.

* cited by examiner

FRACTURE PREDICTION DEVICE FOR SPOT WELDED PORTION, METHOD OF THE SAME, SOFTWARE ARRANGEMENT, AND COMPUTER-ACCESSIBLE MEDIUM

CROSS-REFERENCE TO RELATED APPLICATION(S)

This application is a national stage application of PCT Application No. PCT/JP2005/007100 which was filed on Apr. 12, 2005 and published on Oct. 27, 2005 as International Publication No. WO 2005/100949, the entire disclosure of which is incorporated herein by reference. This application claims priority from the International Application pursuant to 35 U.S.C. §365. The present application also claims priority under 35 U.S.C. §119 from Japanese Patent Application Nos. 2004-118201 and 2005-112644, filed Apr. 13, 2004 and Apr. 8, 2005, respectively.

FIELD OF THE INVENTION

The present invention relates to a fracture prediction device for a spot welded portion, suitable for use for a spot welding of a structural member for an automobile, and in particular, for predicting a fracture of the spot welded portion of a member at a time of a collision deformation, to a method thereof, a software arrangement (e.g., a computer program), and a computer-readable recording medium.

BACKGROUND INFORMATION

Recently, it became problematic for an automotive industry to develop a vehicle structure that is capable of eliminating or significantly reducing an injury for a passenger at a time of a collision. The vehicle structure having such crashworthiness can be obtained such that an impact energy at the time of a collision is absorbed by structural members other than a passenger section, and a deformation of the passenger section is minimized to thereby securing a survival space. Namely, it is important to make the structural members absorb the impact energy.

A main structural member absorbing the impact energy at a full-lap crash or an offset crash of an automobile can be a front side member. In the front side member, the cross section of the member can be closed by a spot welding after the member is formed by a press forming process, etc. Generally, this front side member can be collapsed to thereby absorb the impact energy. It may be beneficial to stabilize a buckling mode and possibly prevent and reduce its bending and/or a fracture halfway, e.g., to improve the absorption of the impact energy.

There may exist certain problems such as a fracture which may occur from a welded point at the time of buckling to cause an unstable buckling mode and the absorption of the impact energy deteriorates, if a spot welding interval, a nugget diameter, and a welding condition are not optimized to stabilize the buckling as for the above-stated spot welding of the member.

Conventionally, a condition has been reviewed to solve a problem, in which, for example, a member is buckled stably without fracturing at a welded point by manufacturing members experimentally while changing spot welding intervals variously, and performing a crash test, as described in Expository Papers No. 9705 JSAE SYMPOSIUM "New Forming Technique of Vehicle Structure".

However, in the above-described method, trial and error should be used in which experimental products are manufactured by each automobile, or by each member to perform the test. Therefore, a problem may exist such that a manufacturing cost becomes high and a long time for design.

In addition, as described in Japanese Patent Application Laid-Open No. Hei 6-182561, a fracture prevention structure of a welded portion of a floor panel where a load is applied is proposed, but it is a structure only for the floor panel. Therefore, it still required trial and error by the experimental products to obtain a spot welding method in which fracture at the welding points is prevented in every impact absorbing member, and the impact energy is absorbed by the stable buckling.

Further, Japanese Patent Application Laid-Open No. 2002-31627 describes an optimization of the spot welding interval. However, it provides only a simple index as for individual spot welding strength, and may not provide an accurate prediction for the fracture as it is. Therefore, a problem exists in which a design based on an accurate fracture prediction for the spot welded portion may be very difficult or even impossible.

As the index of the strength at the spot welded portion, a shear tension test and a cross tension test as described in Specifications JIS Z3136 and JIS Z3137 are representative thereof. The examples under various test modes (assuming various load states other than the above) in general describe that a shear tension test value is treated as a shear strength of the welded portion, and a cross tension test value is treated as a peeling strength of the welded portion by two kinds of tests prescribed in JIS.

However, the shear strength and the peeling strength of the spot welding obtained by the test can come under a structural influence, such as a width. Therefore, the test value cannot help being corrected and estimated from various points of view in an actual member. In a system making an optimal design by a collision simulation of an automobile on a computer which is advancing rapidly in recent years, an estimation accuracy thereof may not be adequate, and a reliability of the optimal design for a collision safety has likely been deteriorated.

SUMMARY OF EXEMPLARY EMBODIMENTS OF THE INVENTION

One of the objects of the present invention is to prevent the fracture of the welded portion of the member at the time of crash deformation, to thereby realize an optimization of a deformed buckling mode. Another object of the present invention is to improve the absorbed energy of the crash by determining a fracture prediction for the spot welded portion at the time of the crash deformation using, e.g., a prediction model implemented in a finite element method analysis by the finite element method analysis on a processing arrangement to limit a use of the experimental manufacturing of the member or the collision test.

Thus, exemplary embodiments of the present invention are provided. According to one exemplary embodiment, a fracture prediction device for a spot welded portion can be provided. Such device can include an input arrangement configured to input all or some of a material strength, a plate thickness, a nugget diameter of a spot welding, a plate width of a joint, and a rotation angle of the joint plates in a tension test, based on a cross tension test and/or a shear tension test at a spot welded joint. A first calculation arrangement can also be provided which may be configured to calculate a fracture strength parameter of the spot welded portion in a cross tension and/or a shear tension from all or any of the material strength, the plate thickness, the nugget diameter of the spot welding, the plate width of the joint, and the rotation angle of the joint in the tension test. Further, a parameter storage arrangement can be included which may be configured to store the fracture strength parameter by each steel type. In addition, a second calculation arrangement may be provide which can be configured to determine a fracture of the spot welded portion by installing the fracture strength parameter stored in the parameter storage arrangement into a fracture prediction formula in which a deformation at a periphery of the spot welding is modeled by a finite element procedure. According to another exemplary embodiment of the present invention, the second calculation arrangement can be configured to determine a fracture strength parameter in a cross tension and/or a shear tension based on a fracture strength curve of a spot welded portion asked from all or some of the material strength, the plate thickness, the nugget diameter of the spot welding, the plate width of the joint, and the rotation angle of the joint in the tension test. The second calculation can further be configured to determine a fracture of the spot welded portion by installing the fracture strength parameter stored in the parameter storage arrangement into a fracture limit line in which a deformation at a periphery of the spot welding is modeled by the finite element procedure.

In addition, method, software arrangement, and computer accessible medium for a spot welded portion can be provided which performs substantially similar functions as the prediction device described herein above.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figure showing illustrative embodiment(s), result(s) and/or feature(s) of the exemplary embodiment(s) of the present invention, in which.

DETAILED DESCRIPTION OF EXEMPLARY EMBODIMENTS OF INVENTION

Figure 1:
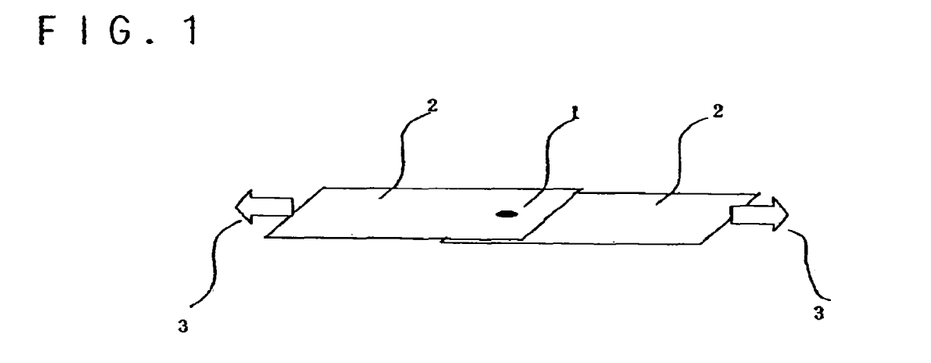
FIG. 1 is an illustration of an outline of a method of a shear tension test according to an exemplary embodiment of the present invention.

Hereinafter, exemplary embodiments of the present invention are described with reference to the drawings. FIG. 1 is an illustration of an outline of a method of a shear tension test. For example, as a specimen, two steel plates being base materials 2 can be overlapped and spot welded as shown in FIG. 1 to form a nugget 1. A tension test for such exemplary specimen in directions shown by arrows 3 can be performed until this specimen fractures. At this time, displacements and loads of the specimen in the tensile directions 3 may be measured. The fracture can occur at a periphery of the nugget 1, and it can become a maximum load at such time. This value can be a fracture limit load "Ftss" (N). When it reaches this limit load "Ftss", a mean stress "σo" (MPa) inside of the base material can be "Ftss/W·t" from a width "W" (mm) and a plate thickness "t" (mm) of the base material 2.

At the periphery of the nugget 1 which is an initiation point of the fracture, a stress concentration factor "α" at an end portion of the nugget 1 and the base materials 2 can be defined as shown in a formula (1) as a fraction of a tensile strength "TS" of the base material and the mean tensile stress "σo" of the base material when a maximum stress is assumed to reach the tensile strength "TS" (MPa).

$$\alpha = TS/\sigma o = TS \cdot W \cdot t/Ftss \qquad (1)$$

The fracture limit loads "Ftss" can be measured by materials with various tensile strengths "TS" and various specimen widths "W", plate thicknesses "t", and nugget diameters "d" (mm). Thus, this stress concentration factor "α" can be calculated using formula (1) to create a table as a database. The fracture limit load "Ftss" with an arbitrary tensile strength "TS", plate thickness "t", width "W", and nugget diameter "d" can be predicted with a formula (2) by using the stress concentration factor "α" in the table.

$$Ftss = TS \cdot W \cdot t/\alpha \qquad (2)$$

Further, the stress concentration factor "α" can become a curve by organizing with a fraction "d/W" of the nugget diameter "d" and the width "W". Therefore, the "Ftss" may be predicted using formula (2) by using the "α" calculated from formula (3).

$$\alpha = k/(p \cdot d/W - q)^n + r \qquad (3)$$

k, p, q, n, and r can be the parameters to perform a fitting of a curvilinear relation of the "α" and the "d/W" using formula (3). These parameters can preferable to be in the ranges as follows: k=0.001 to 100; p=0.01 to 100; q=−10 to 10; n=1 to 10; and r=−100 to 100. However, an exemplary formula can remove or limit the need to make the fitting of the curve to have a format of formula (3), and it may be a formula capable of fitting the curvilinear relation. In addition, "α" may be read from the graph of the curve directly without using formula (3).

Next, a member in an arbitrary shape welded by the spot welding can be modeled by using a finite element procedure, e.g., using a processing arrangement (e.g., a computer). A shear force "Fs" (N) in a direction along a member surface of an element connecting members with each other in which the spot welding may be modeled. A vertical force "Fn" (N) in a direction connecting members with each other orthogonal to the shear force "Fs" (N) can be calculated by the processing arrangement one after another during a deformation of a collision analysis reproduced by using the finite element method. This calculation arrangement of the "Fs" and "Fn" can depend on a general analysis code, for example, refer to "PAM-CRASH v2002 user's manual" made by ESI Co., Ltd. A fracture judgment on the processing arrangement can be set at the time when formula (4) becomes true.

$$Fn^2 + Fs^2 \geq Ftss^2 \quad (4)$$

Figure 2:
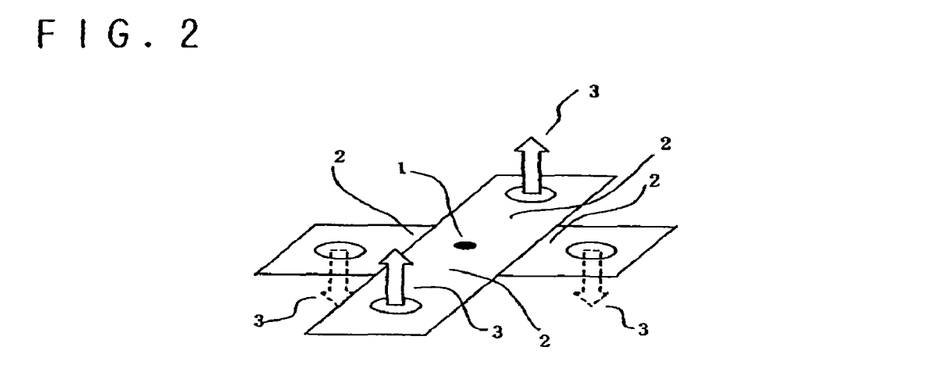
FIG. 2 is an illustration of an outline of a method of a cross tension test according to an exemplary embodiment of the present invention.
Figure 3:
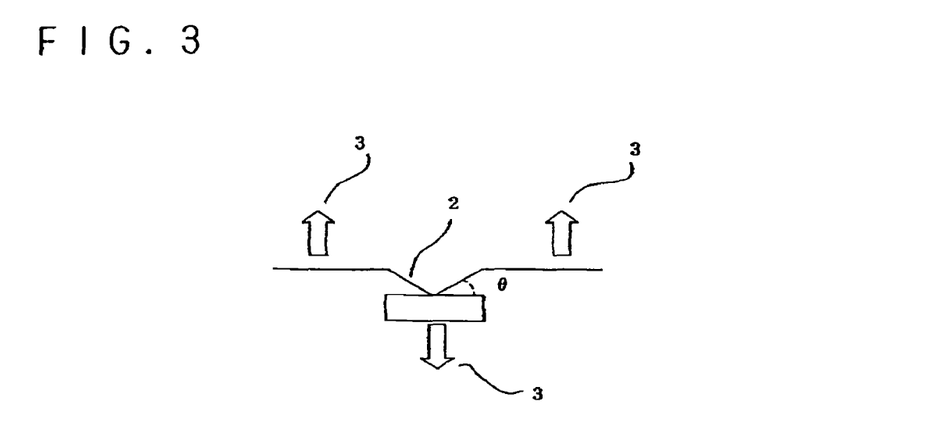
FIG. 3 is a side view at a testing time of the cross tension test of FIG. 2.

FIG. 2 is an illustration of an outline of a method of a cross tension test according to the exemplary embodiment of the present invention. The specimen includes two steel plates that are the base materials 2 overlapped and spot welded as shown in FIG. 2 to form the nugget 1. A tension test for this specimen can be performed in the directions shown by the arrows 3 until this specimen fractures. At such time, the displacements and the loads of the specimen in the tensile directions 3 may be measured. The fracture can occur at the periphery of the nugget 1, and it may be considered the maximum load at this time. This value can be set as a fracture limit load "Fcts" (N). When it reaches this limit load "Fcts", the mean stress "σo" (MPa) inside of a plate surface of the base material can be "Fcts/(2W·t·sin θ)" from the width "W" (mm) and the plate thickness "t" (mm) of the base material 2 using an angle "θ" shown in FIG. 3.

At the periphery of the nugget 1 which is intended to be the initiation point of the fracture, the stress concentration factor "α" at the end portion of the nugget 1 and the base material 2 can be defined using formula (5) as the fraction of the tensile strength "TS" (MPa) of the base material and the mean tensile stress "σo" (MPa) of the base material if the maximum stress is assumed to reach the tensile strength "TS" (MPa).

$$\alpha = TS/\sigma o = TS \cdot W \cdot t / Fcts \quad (5)$$

Formula 5 has the same format as formula (1) polled by the shear tension test, and an angle correction "θ" is added because the tensile directions are different. Consequently, the fracture limit load "Fcts" can be calculated using formula (6) with an arbitrary material, width, plate thickness, and nugget diameter using, e.g., the same or similar procedure as the shear tension test.

$$Fcts = 2 \cdot TS \cdot W \cdot t \cdot \sin \theta / \alpha \quad (6)$$

As same as the case in the shear tension, a fracture judgment of the spot welded portion in an arbitrary member at the time of the collision deformation is regarded to be at the time when a formula (7) becomes true on the processing arrangement.

$$Fn \geq Fcts \quad (7)$$

As described above, the fracture limit loads, that is fracture strength parameter "Ftss" and "Fcts" can be calculated by formulas (1)-(3), (5) and (6), the collision deformation may be analyzed by the finite element procedure with the arbitrary member, and the fracture judgment of the spot welding is set to be at the time when formula (4) and/or formula (7) becomes true first or when they become true at the same or similar time or a formula into which formula (4) and formula (7) can be combined becomes true.

When the form of the deformation is known from the shape of the member and an input method of the load, e.g., one of formula (4) or formula (7) may be calculated on the processing arrangement to make a determination. Besides, the fraction between the "Fn" and the "Fs" is calculated on the processing arrangement one after another, and the fracture determination may be made, for example, by using formula (7) when Fn>3Fs, and formula (4) in certain other cases.

Thus, it is possible to predict the fracture judgment of the spot welding on the processing arrangement accurately, e.g., without verifying by creating the member and performing the collision test actually. According to an exemplary embodiment of the present invention, it is possible to investigate a condition in which the spot welding does not fracture by varying the member shape, the material, the plate thickness, the nugget diameter, and a welding position on the computer by using this procedure, and an optimal member can be designed.

As for the fracture limit load of the spot welding, e.g., when the tensile strength "TS" of the material is larger than 590 (MPa), it can be suitable to calculate the "Ftss" in the shear tension test by using the following formula (2'), formula (3m) instead of the formula (2), formula (3), and the "Fcts" in the cross tension test by using the following formula (3m2), formula (3m3), formula (3m4), and formula (6') instead of the formula (3), formula (6), different from the above-described procedure.

$$Ftss = TS \cdot W \cdot t / \alpha_1 \quad (2')$$

$$\alpha_1 = (e(TS/f-g)^h - i)/(d/W)^j + 1 \quad (3m)$$

e, f, g, h, i, and j are parameters to perform a fitting of a curvilinear relation of the "$\alpha_1$" and the "d/W" with the formula (3m), and they are within the ranges as follows: e=0.0001 to 100; f=100 to 2500 (MPa); g=0.1 to 10; h=0.0001 to 10; i=0.01 to 100; and j=1 to 100.

$$Fcts = 2 \cdot TS \cdot W \cdot t \cdot \sin \theta / \alpha_2 \quad (6')$$

$$\alpha_2 = \beta/(d/W)\chi + \delta \quad (3m2)$$

$$\chi = \phi(TS/\gamma - \eta)^\Psi - \xi \quad (3m3)$$

$$\delta = \lambda(TS/\mu - \rho)\omega - \zeta \quad (3m4)$$

$\beta,\chi,\delta,\Phi,\gamma,\eta,\Psi,\xi,\lambda,\mu,\rho,\omega$, and $\zeta$ are parameters to perform a fitting of a curvilinear relation of the "α2" and the "δ/W" with the formula (3m2), formula (3m3), and formula (3m4), and they are within the ranges as follows: β=0.0001 to 100; γ=0.1 to 100; γ=100 to 2500 (MPa); η=0.1 to 10; Ψ=0.0001 to 100; ξ=0.01 to 100; λ=0.01 to 100; μ=100 to 2500 (MPa); ρ=0.1 to 10; ω=0.0001 to 100; and ζ=0.01 to 100.

A formula to make the fitting of the curve is not needed to be the formats of these exemplary formulas, and it may be used to make the fitting of the curvilinear relation. Further, the curvilinear relation of the "α1" or the "α2" and the "δ/W" can become one curve by each strength grade without using these formulas, and therefore, the "α1" or the "α2" can be identified directly from each graph of the curve.

Figure 4:
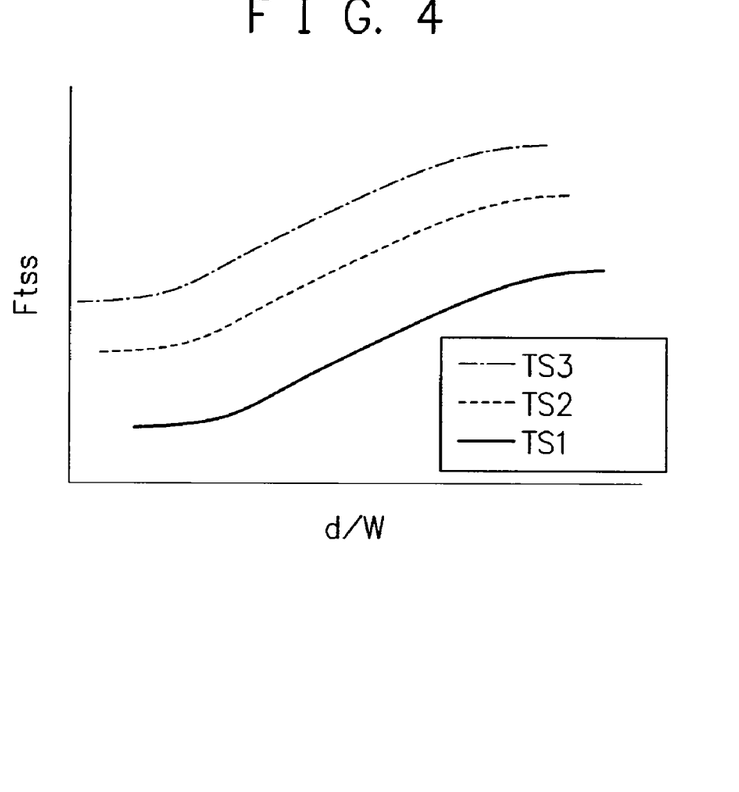
FIG. 4 is a graph of exemplary fracture strength curves.

FIG. 4 is a view schematically showing a method to calculate the fracture limit load by using a graph based on experimental data, in addition to the method to calculate the fracture limit load by using the formulas such as formula (1), formula (2), formula (3), and formula (5), formula (6), or the formula (3m), formula (3m2), formula (3m3), and formula (3m4) instead of the formula (3). The fracture limit loads can be measured by the test in which the "δ/W" is varied and when it is graphed, the fracture strength curves can be written in various curvilinear relations depending on the material strength TS.

In this manner, the material strengths can be TS1<TS2<TS3. The fracture limit load corresponding to the condition can be identified from these curves directly. This curve becomes a fracture limit load curved surface by taking the plate thickness "t" as a third axis, and the fracture limit load can be identified by reading a value on the curved surface at an arbitrary plate thickness "t", the material strength "TS", the width "W", and the nugget diameter "d".

Figure 5:
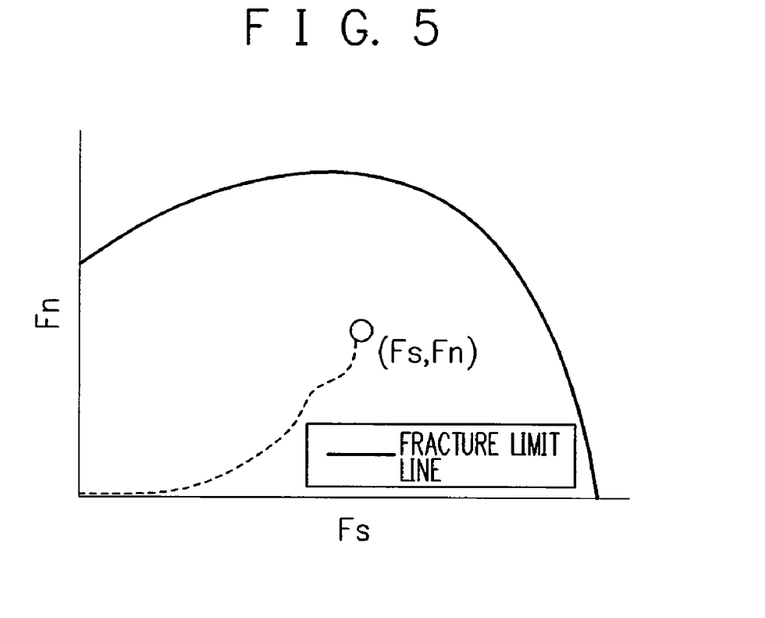
FIG. 5 is a graph of an exemplary relation between a fracture limit line and calculated strengths Fn, Fs.

Further, a fracture limit line can be created as shown in FIG. 5 by using the fracture limit loads identified by the various rotation angles "q" instead of using formula (4) and formula (7). This fracture limit line and the "Fn", "Fs" calculated one after another by the analysis of the finite element method may be compared, and it may be judged as the fracture when the "Fn", "Fs" come to on the curve and at outside of the curve.

This exemplary procedure can be applied not only to steel material but also to every other material. Further, such procedure can be applied not only to every welding such as a laser welding, an arc welding, a seam welding, and a mash-seam welding, but also to the spot welding, and further, to every mechanical bonding such as a TOX bonding and a rivet bonding, a friction bonding, a diffusion bonding, a friction diffusion bonding, a friction stir welding and every bonding by using an adhesive agent. The calculation procedure on the processing arrangement can be applied to a boundary element procedure, a difference procedure, a meshless procedure, an elementary analysis, and every calculation procedure without limiting to the finite element procedure, and it can be applied to a calculation procedure independent of a material mechanics and the processing arrangement.

The calculation procedure of the stress concentration factor "α" using the experiment is not also limited to the above-stated shear tension test, cross tension test, and it can be calculated using every shape of specimen, and a load applying procedure.

The above-stated prediction of the fracture judgment can be applied not only to the collision analysis of the whole automobile and member, but also to components other than the automobile, and it goes without saying that it can be applied to an analysis in a quasi-static deformation other than a collision.

Figure 8:
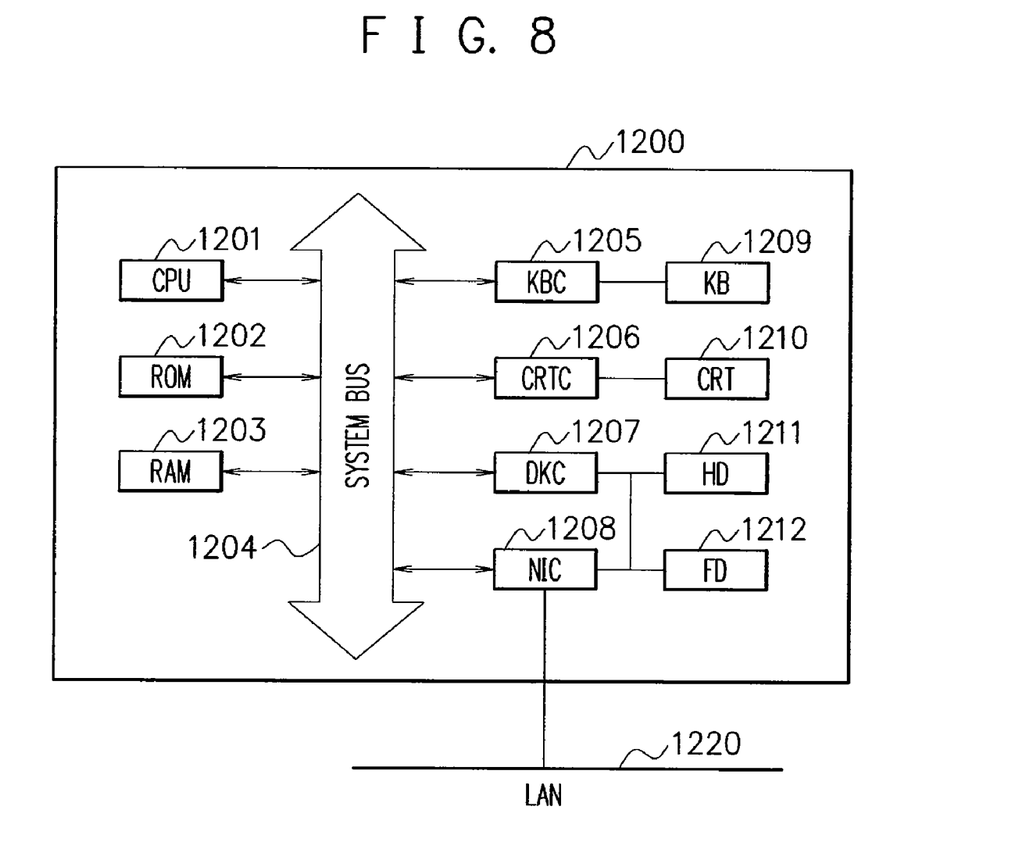
FIG. 8 is a block diagram showing an exemplary computer system capable of configuring a fracture prediction device for a spot welded portion according to an exemplary embodiment of the present invention.

FIG. 8 is a block diagram showing an example of a computer system capable of configuring a fracture prediction device for a spot welded portion. In FIG. 8, a reference numeral 1200 is a computer PC. The PC 1200 includes a CPU 1201, can execute a device control software stored in a ROM 1202 or a hard disk (HD) 1211, or supplied from a flexible disk drive (FD) 1212, and may controls respective devices connected to a system bus 1204.

Respective function arrangement of an exemplary embodiment according to the present invention are constituted by, e.g., programs stored in the above-stated CPU 1201, ROM 1202, or hard disk (HD) 1211 of the PC 1200.

Reference numeral 1203 is a RAM, and can function as a main memory, a work area, etc. of the CPU 1201. Reference numeral 1205 is a keyboard controller (KBC), and it may control input signals inputted from a keyboard (KB) 1209 to the system main body. Reference numeral 1206 is a display controller (CRTC), and can perform a display control on a display device (CRT) 1210. Reference numeral 1207 is a disk controller (DKC), and it can control an access with the hard disk (HD) 1211 and the flexible disk (FD) 1212, storing a boot program (a program starting an execution (operation) of hard-wares and softwares of a personal computer), plural application programs, edit files, user files, network management programs, and so on.

Reference numeral 1208 is a network interface card (NIC), and can perform interactive data exchanges with a network printer, other network devices, or other PCs via a LAN 1220.

The above-described functions of the exemplary embodiment of the present invention can also be obtained by an execution of the program by the processing arrangement. Besides, an arrangement configured to supply the processing arrangement with the computer program, for example, a computer readable recording medium or computer accessible medium such as a CD-ROM, etc. which is configured to record such program, or a transmission medium such as an internet transmitting the program can be utilized as an exemplary embodiment of the present invention. Further, a computer program product such as the computer readable recording/accessible medium which records the above-described program can also be utilized as an exemplary embodiment of the present invention. The above-described computer program, recording medium, computer accessible medium, transmission medium, and computer program product can be utilized according to an exemplary embodiment of the present invention. As the recording media, for example, a flexible disk, a hard disk, an optical disk, a magnetic optical disk, a CD-ROM, a magnetic tape, a nonvolatile memory, a ROM, etc. can be used.

EXAMPLE 1

An exemplary embodiment of a system is according to the present invention can be structured in which the above-stated fracture prediction model is used, and a fracture of a spot welded portion is judged automatically while analyzing a collision deformation of a member, as a subroutine program in a general collision analysis FEM code. The used code is "PAM-CRASH v2002" made by ESI Co., Ltd., and the spot welded portion is modeled by using a "Multi-PLINK" as for the member modeled by a shell element.

A comparison of an analysis, in which a shear tension test and a cross tension test are modeled as they are, and an experiment is the best for an accuracy verification of the fracture prediction model, because an exact comparison becomes possible. Therefore, a shear tension specimen and a cross tension specimen are created with a steel plate of 590 MPa grade and a thickness "t"=1.8 (mm), according to JIS standards of 3136, 3137. A nugget diameter of the spot welding is $5\sqrt{t}$ (mm). A test is performed by using an Instron type testing machine, and loads and displacements until a spot welded portion fractures are measured at that time. At the same time, the shear tension test and the cross tension test in the same forms as the test are modeled on the processing arrangement, an analysis of the tension test is performed by the FEM code mounting the above-stated subroutine program to judge the fracture of the spot welded portion automatically, and the loads and the displacements until the spot welding fractures as same as the experiment are calculated. Inputted initial parameters of "TS"=642 (MPa), "t"=1.8 (mm), "d"=6.7 (mm), "θ"=23°, are set as common parameters. In the shear tension test, the following values are used.

"α"=1.80(−), "W"=40 (mm)

In the cross tension test, the following values are used.

"α"=2.17(−), "W"=50 (mm)

The fracture strength parameters "Ftss"=25680 (N), "Fcts"=20798 (N) obtained by the above are installed in a fracture prediction formula in which a deformation at a periphery of the spot welding is modeled by the finite element method, to thereby judge the fracture of the spot welded portion.

The test model may be generated by the shell element of which collision analysis level of a full vehicle is rough, and a boundary condition is also simplified with considering that they can be applied for the collision analysis of an actual member.

Figure 6:
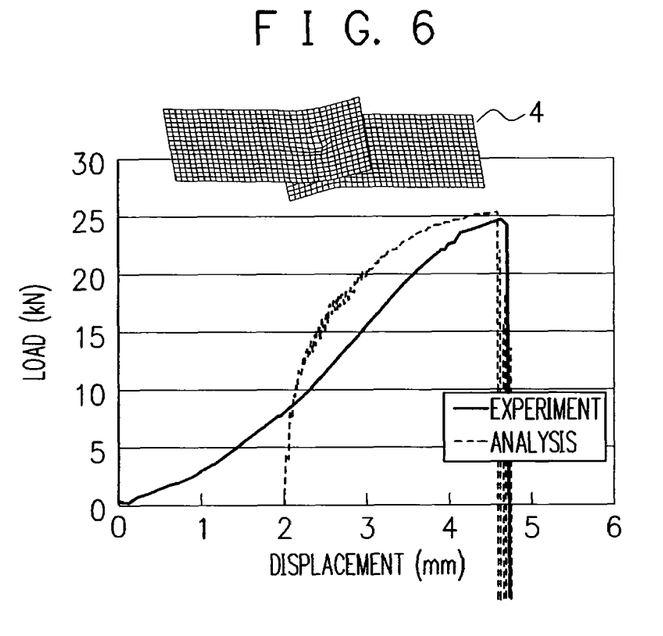
FIG. 6 is a graph comparing relationships of a load and a displacement at a time of fracture in the shear tension test with an experiment and a simulation, e.g., FEM.
Figure 7:
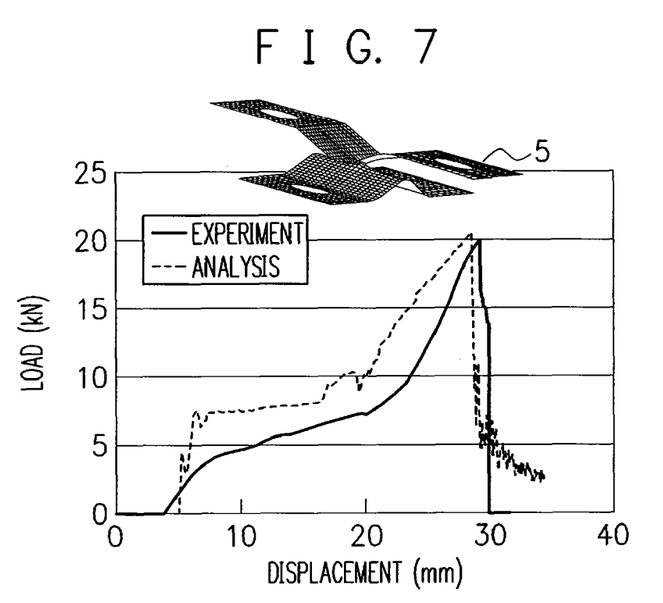
FIG. 7 is a graph showing relationships of a load and a displacement at a time of a fracture in the cross tension test with an experiment and a simulation, e.g., FEM.

FIG. 6 and FIG. 7 are graphs of examples for verifying this exemplary system. Reference numeral 4 represents a simulation of a shear tension specimen, and reference numeral 5 represents a simulation of a cross tension specimen. Fracture modes are respectively different in the shear tension test and the cross tension test. However, the fracture loads on the load—stroke curves of the experiment and the FEM analysis are matched. In the shear tension test, it seems that the shapes of the load—displacement curves until they reach the fracture load are different between in the experiment and the analysis. However, they appear to be different because a specimen chuck is connected to a crosshead via a universal joint in the experiment, and therefore, a rotation of the chuck portion occurs at a time of load rising, but this rotation is not considered in the analysis because of the simplification of the model. This may just change a behavior of an initial stroke change, and therefore, it does not essentially affect on the load at the time of the fracture occurrence.

Behaviors of the load—displacement curves are slightly different between in the experiment and in the analysis also in the cross tension test, but it is similarly a problem of the chuck of the experiment. Therefore, it only affects on the initial behavior and the experiment and the analysis are matched at the fracture loads. Of course, if it is modeled with including the chuck portion on the analysis, the behavior of this portion may be matched with the experiment, but here, it is skipped because it is not an essential problem. This shows that it is possible to predict the spot fracture accurately in an analysis at practical level in which detailed portions are simplified in a large-scaled collision analysis of an entire model or a partial model of the full vehicle, because the fracture load of an actual test can be predicted accurately even by the FEM analysis in which the test is modeled in a simple manner.

As described above, the analysis procedure capable of predicting the fracture of the spot welding accurately by a basic test can be utilized. Further, the prediction of the spot welding fracture at the time of the collision deformation in a component level can be verified from both experimentally and using an exemplary analysis, and it is confirmed that the fracture prediction in the analysis is matched with the experiment. The system is confirmed to be a system capable of controlling and designing a deformation mode of members and an absorption energy based on the above, because the fracture of the spot welded portion can be predicted.

This procedure can be installed to general solver processing arrangements, such as "LS-DYNA3D" made by LSTC Co., Ltd., "RADIOSS" made by MECALOG Co., Ltd., and to a solver developed individually, in addition to the general solver "PAM-CRASH". Further, the model and procedure of the spot welded portion may be applicable for a beam element, a shell element, a solid element, and so on, in addition to a contact type such as the "Multi-PLINK".

EXAMPLE 2

Figure 9:
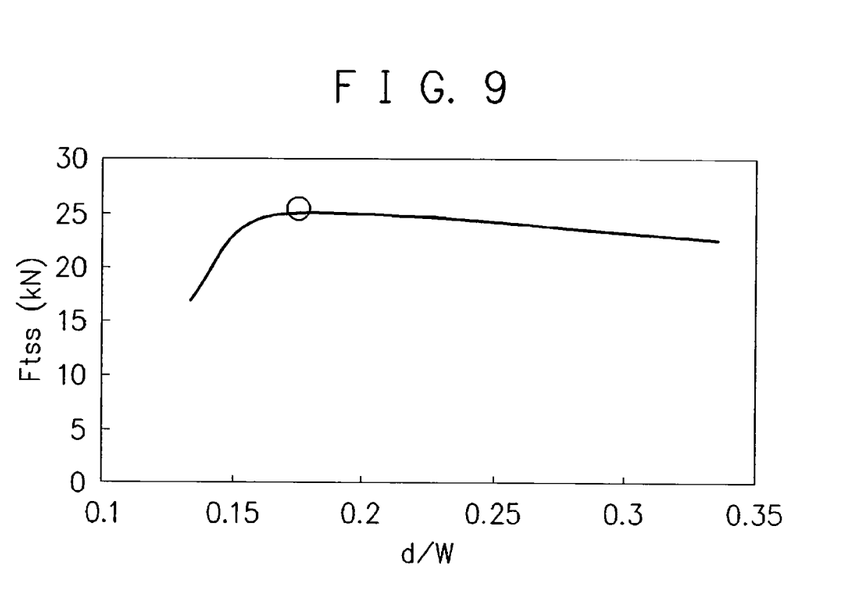
FIG. 9 is a graph showing a fracture strength curve of an actual exemplary steel plate of 590 MPa grade, and a thickness of 1.8 mm.

A verification of a prediction accuracy of a shear tensile strength is performed by using a fracture strength curve. Material thereof can be a steel plate of 590 MPa grade, a thickness=1.8 (mm) as same as described in Example 1. Initially, a width "W" of a specimen of the shear tension test can be varied from 20 (mm) to 50 (mm), at the same time, a nugget diameter "d" is also varied from 4 (mm) to 7 (mm) to perform the test, and a fracture strength parameter "Ftss" is actually measured. An exemplary fracture strength curve shown in FIG. 9 can be obtained from the results of the test. The fracture strength parameter "Ftss"=25.5 (kN) can be read from the fracture strength curve as shown by a circular sign in FIG. 9, under a condition of "d"=6.7 (mm), "W"=40 (mm) which is the same condition as in the example 1. This is approximately the same value with the "Ftss" under the same condition in the example 1. The fracture loads are generally matched on the load—stroke curves of the experiment and the FEM analysis as shown in FIG. 6, by performing a finite element method (FEM) analysis in the following, in which the test is modeled as same as in the example 1. Consequently, FIG. 6 shows that the fracture strength parameters under any condition in practical use can be obtained by creating the fracture strength curve with varying the width "W" and the nugget diameter "d" within a wide range corresponding to the actual use. The case when the material strength and the plate thickness are fixed is shown in the above, but when the strength and the plate thickness vary, the fracture strength curves are to be created respectively.

EXAMPLE 3

In addition, an exemplary system can be structured such that a fracture prediction model when a tensile strength thereof is larger than 590 MPa grade is used, and a fracture of a spot welded portion is automatically judged while analyzing a collision deformation of a member as a subroutine program in the general collision analysis FEM code. The used code is "PAM-CRASH v2003" made by ESI Co., Ltd., and the spot welded portion of a member which is modeled by a shell element is modeled by using "Multi-PLINK".

Figure 10:
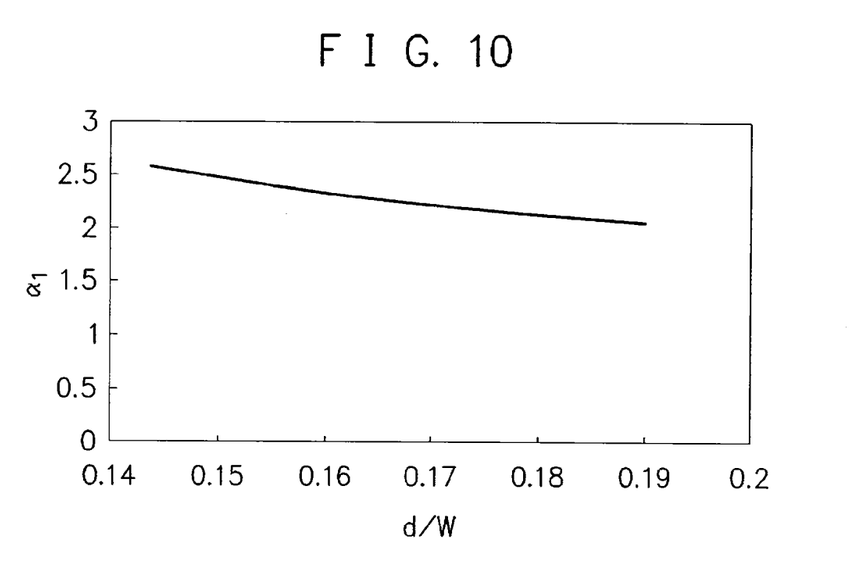
FIG. 10 is a graph showing an exemplary curvilinear relation of "$\alpha_1$" and "d/W" identified by an experiment.

A comparison of an analysis, in which the shear tension test can be modeled as is, and an experiment is preferable for an accuracy verification of the fracture prediction model, because an exact comparison becomes possible. Therefore, a shear tension specimen can be created with a steel plate of 980 MPa grade and a thickness "t"=1.4 (mm) as same as in the example 1. A nugget diameter of the spot welding is $6\sqrt{t}$ (mm). A test may be performed using an Instron type testing machine, and the loads and the displacements until the spot welded portion fractures are measured. At such time, the shear tension test in the same form as the test can be modeled on the processing arrangement, an exemplary analysis of the tension test is performed by the FEM code mounting the above-stated subroutine program to judge the fracture of the spot welded portion automatically, and the loads and displacements until the spot welding fractures as same as the experiment are calculated. Inputted initial parameters of "TS"=983 (MPa), "t"=1.4 (mm), "d"=7.2 (mm), "θ"=23°, "α1"=2.12 (–), and "W"=40 (mm) are used. The "α1" is determined by reading from a graph of the curve of the "α1" and the "δ/W" asked by the experiment as shown in an exemplary graph of FIG. 10. A fracture strength parameter "Ftss"=26340 (N) obtained by the above is installed to a fracture prediction formula in which a deformation at a periphery of the spot welding is modeled by a finite element method, to judge the fracture of the spot welded portion.

The test model can be created by a shell element of which collision analysis level of a full vehicle is rough, and a boundary condition is also simplified with considering that they can be applied for the collision analysis of an actual member.

Figure 11:
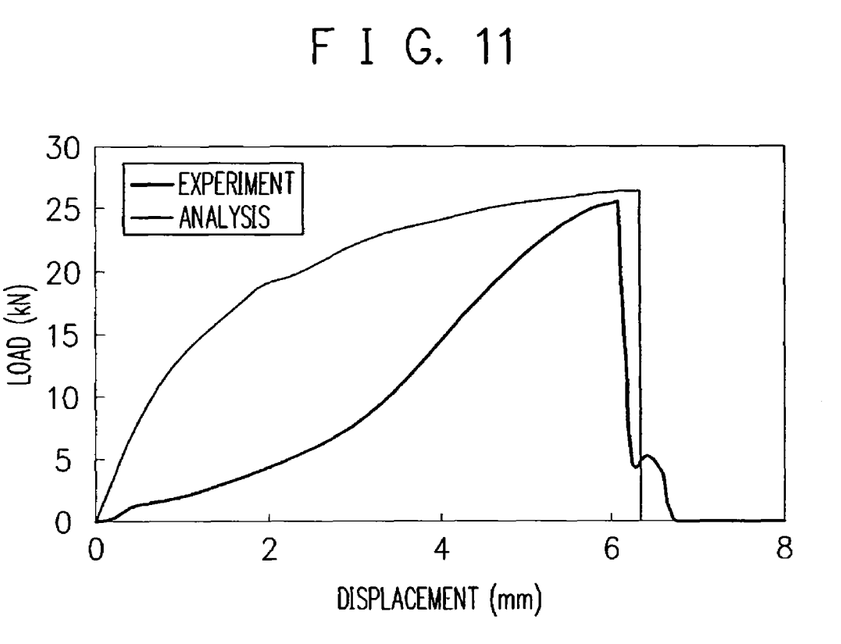
FIG. 11 is a graph in which relations between a load and a displacement at a time of fracture in the shear tension test with a high strength steel of 980 MPa grade, are compared with an experiment and a simulation (FEM)

FIG. 11 shows a graph of a verification of this exemplary system, which demonstrates that the fracture loads on the load—stroke curves of the experiment and the FEM analysis can be matched in the shear tension test. The shapes of the load—displacement curves until they reach the fracture loads are different between the experiment and the analysis in the shear tension test, but the cause is the same or similar as the cause indicated in the example 1, without problems.

Figure 12A:
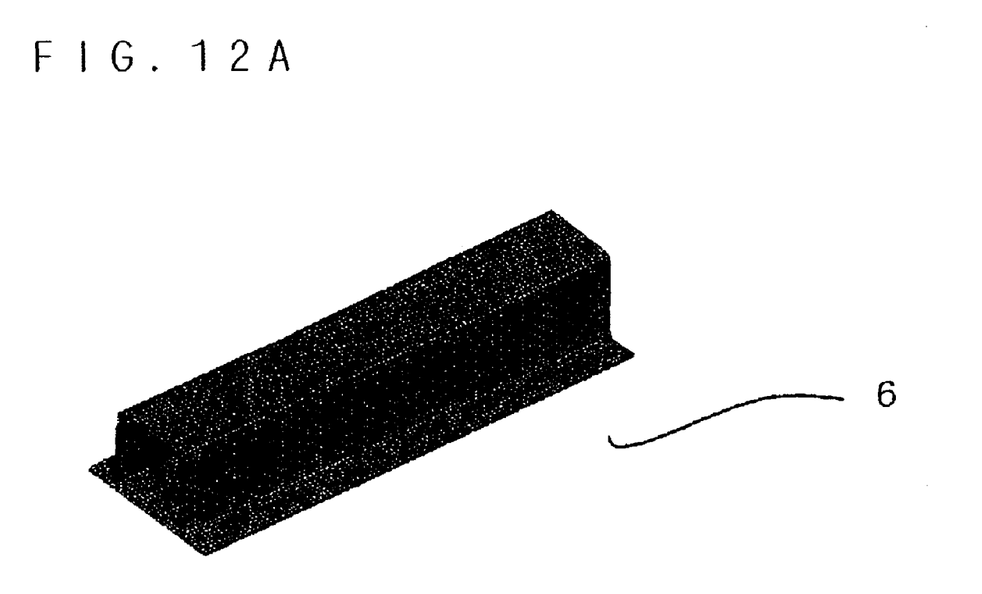
FIG. 12A is an illustration of an exemplary member shape of the high strength steel of 980 MPa grade used for a dynamic axial crush test.

Further, a verification of a prediction model can be performed by an axial crush test of a simple member. As shown in an exemplary illustration of FIG. 12A, a member 6 can be constituted by a spot welding of a hat shape in cross section and an attached closure plate, and a hat top portion, perpendicular walls are 50 (mm) respectively, flanges are 20 (mm), and a length in a crush direction is 300 (mm). Exemplary material used for the member is a steel product of 980 MPa grade may be same as the above, and the nugget diameter of the spot welding is $4\sqrt{t}$ (mm). A dynamic crush test can be performed under a condition that a weight of a drop hammer is 500 (kg), an initial speed at the time of the crush is 6 (m/s), and the FEM analysis is performed under the same condition.

Figure 12B:
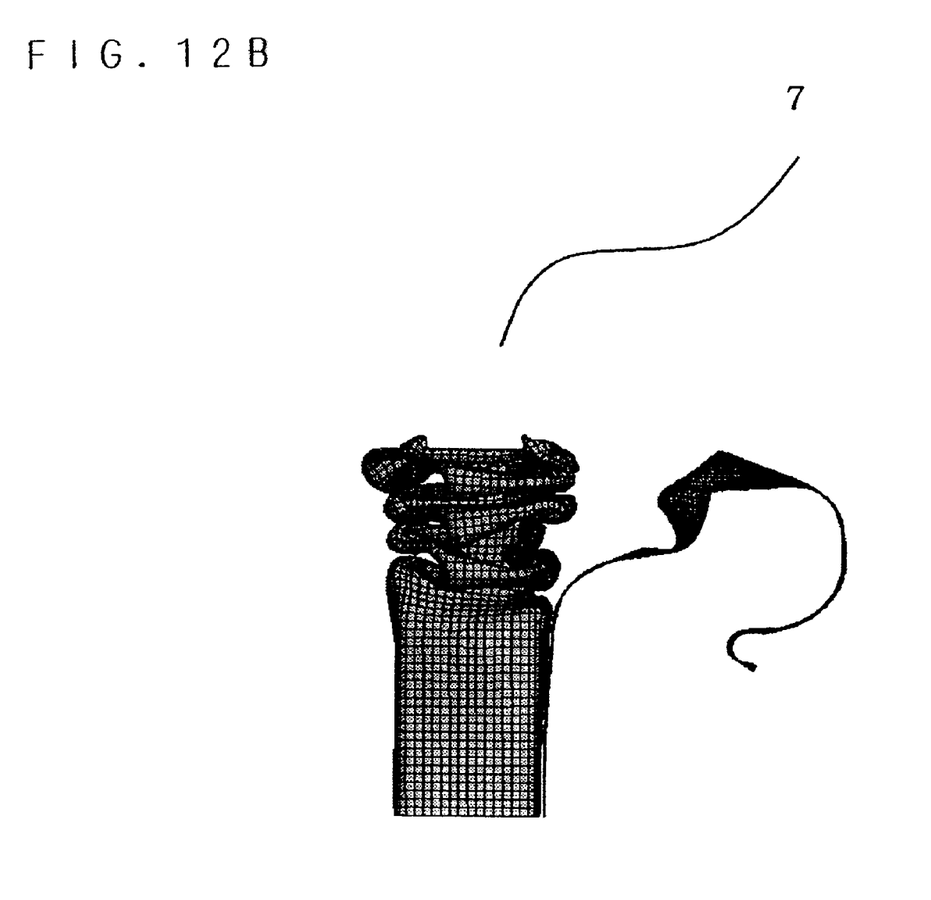
FIG. 12B is an illustration of an exemplary result in which a fractured appearance of an exemplary spot welded portion at the time of a dynamic axial crush test is simulated (FEM)
Figure 12C:
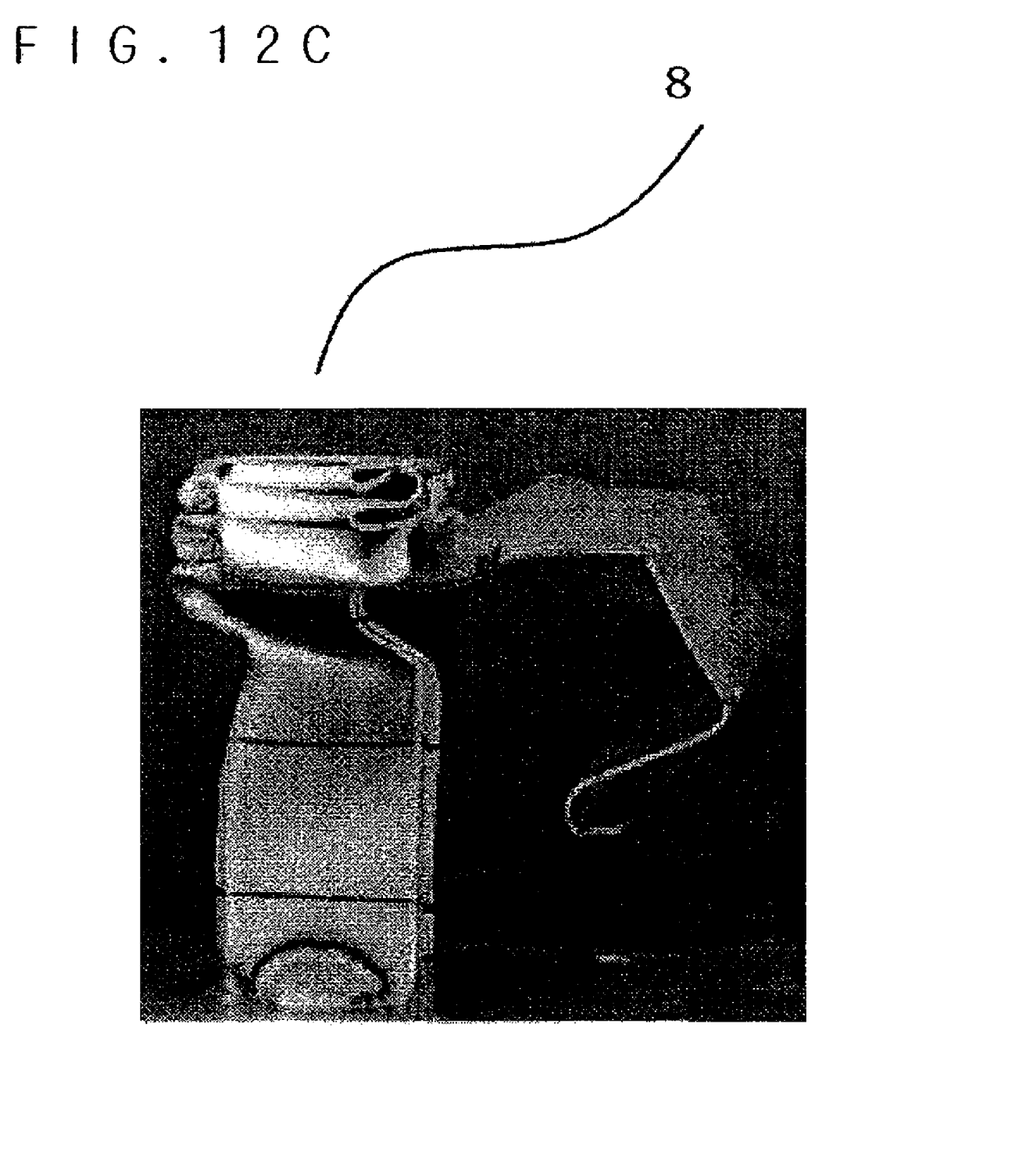
FIG. 12C is an exemplary illustration of a fractured appearance of the spot welded portion at the time of the dynamic axial crush test.

The exemplary test result and the exemplary FEM analysis result can be compared by the shapes of the members after the crush as shown in FIG. 12B showing a simulation 7, and FIG. 12C showing an actual experiment. As a result, shapes of buckling are the same, and in particular, both patterns can be matched in which the spot welded portion fractures, and thereby, the attached closure plate may be detached. Herewith, it is shown that the spot fracture can be predicted accurately by an analysis at practical level in which detailed portions are simplified, in a large-scaled collision analysis of an entire model and a partial model of a full vehicle.

INDUSTRIAL APPLICABILITY

According to exemplary embodiments of the present invention, it is possible to perform a fracture prediction accurately at a portion in which, for example, a spot welding of an automobile member is modeled by a finite element method analysis on a computer. Therefore, a verification of the fracture of the spot welded portion at a time of a collision test by using an actual automobile member can be skipped, and/or the number of times of the verification test can be reduced drastically. Further, for example, experimental manufactures with varying a spot welding condition of the automobile member, a member design preventing or reducing the spot welding fracture using a large-scaled experiment of a collision test, can be replaced by a design preventing or reduce the fracture of the spot welded portion by the collision analysis using the processing arrangement. Therefore, it is possible to contribute to a significant cost reduction and a shortening of a design and development period.

What is claimed is:

1. A fracture prediction device for use with a spot welded portion, comprising:
   an input arrangement configured to input at least one of a tensile strength (TS) of a material, a plate thickness t, a nugget diameter d of a spot welding, a plate width w of a particular joint, or a rotation angle θ of the joint plates in a tension testing procedure which is at least one of a cross tension testing procedure or a shear tension test procedure at a spot welded joint;
   a first calculation arrangement configured to determine a fracture limit load (Fcts) as a fracture strength parameter of the spot welded portion in a cross tension using a formula (a) and a fracture limit load (Ftss) as a fracture strength parameter of the spot welded portion in a shear tension using a formula (b), based on a stress concentration factor α and at least one of the inputted tensile strength TS of the material, the plate thickness t, the nugget diameter d of the spot welding, the plate width w of the joint, or the rotation angle θ of the particular joint in the tension testing procedure, wherein the stress concentration factor α is at least one of (i) defined by a formula of (TS)/(mean tensile stress σo) or (ii) calculated using a stress concentration factor calculation formula, and wherein $$Fcts = 2TSWt \sin\theta/\alpha \qquad (a)$$

$$Ftss = TSWt/\alpha \qquad (b);$$

a parameter storage arrangement configured to store the fracture strength parameter by each steel type; and
   a second calculation arrangement configured to analyze a fracture of the spot welded portion by providing the fracture strength parameter stored in the parameter storage arrangement into a fracture prediction formula in which a deformation at a periphery of the spot welding portion is modeled by a finite element procedure,
   wherein the fracture prediction formula is based on a shear force and a vertical force with respect to the spot welded portion.

2. The fracture prediction device of claim 1, wherein the shear force is provided in a direction along a member surface of an element that connects members with each other in which the spot welding is modeled, and the vertical force is provided in a direction that connects members with each other orthogonally to the shear force.

3. The fracture prediction device of claim 1, wherein the shear force is determined one after another during a deformation of a collision analysis reproduced using the finite element procedure.

4. A fracture prediction device provided for a spot welded portion, comprising:
   an input arrangement configured to input at least one of a tensile strength (TS) of a material, a plate thickness t, a nugget diameter d of a spot welding, a plate width w of a particular joint, or a rotation angle θ of the joint plates in a tension testing procedure which is at least one of a cross tension testing procedure or a shear tension testing procedure at a spot welded joint;
   a first calculation arrangement configured to determine a fracture limit load (Fcts) as a fracture strength parameter of the spot welded portion in a cross tension, using a formula (a), and a fracture limit load (Ftss) as a fracture strength parameter of the spot welded portion in a shear tension using a formula (b), based on a stress concentration factor α and at least one of the inputted tensile strength TS of the material, the plate thickness t, the nugget diameter d of the spot welding, the plate width w of the joint, or the rotation angle θ of the particular joint in the tension testing procedure, wherein the stress concentration factor α is at least one of (i) defined by a formula of (TS) / (mean tensile stress σo) or (ii) calculated using a stress concentration factor calculation formula, and wherein $$Fcts = 2TSWt \sin\theta/\alpha \qquad (a)$$

$$Ftss = TSWt/\alpha \qquad (b);$$

a parameter storage arrangement configured to store the fracture strength parameter by each steel type; and
   a second calculation arrangement configured to analyze a fracture of the spot welded portion by providing the fracture strength parameter stored in the parameter storage arrangement into a fracture limit line in which a deformation at a periphery of the spot welding portion is modeled by a finite element procedure, wherein the fracture limit line is created as a curve based on a shear force and a vertical force with respect to the spot welded portion.

5. The fracture prediction device of claim 4, wherein the shear force is provided in a direction along a member surface of an element that connects members with each other in which the spot welding is modeled, and the vertical force is provided in a direction that connects members with each other orthogonally to the shear force.

6. The fracture prediction device of claim 4, wherein the shear force is determined one after another during a deformation of a collision analysis reproduced using the finite element procedure.

7. The fracture prediction device of claim 4, wherein the fracture strength curve provides a graphic representation written by measuring the fracture strength parameter by a test in which at least one of the material strength, the plate thickness, the nugget diameter of the spot welding, the plate width of the joint, or the rotation angle of the particular joint in the tension testing procedure are varied.

8. A fracture prediction method provided for a spot welded portion, comprising:

inputting at least one of a tensile strength (TS) of a material, a plate thickness t, a nugget diameter d of a spot welding, a plate width w of a particular joint, or a rotation angle $\theta$ of the particular joint in a tension test which is at least one of a cross tension testing procedure or a shear tension testing procedure at a spot welded joint;

determining a fracture limit load (Fcts) as a fracture strength parameter of the spot welded portion in a cross tension using a formula (a), and a fracture limit load (Ftss) as a fracture strength parameter of the spot welded portion in a shear tension using a formula (b), based on a stress concentration factor $\alpha$ and at least one of the inputted tensile strength TS of the material, the plate thickness t, the nugget diameter d of the spot welding, the plate width w of the joint, or the rotation angle $\theta$ of the joint in the tension testing procedure, wherein the stress concentration factor $\alpha$ is at least one of (i) defined by a formula of ( TS)/(mean tensile stress $\sigma o$) or (ii) calculated using a stress concentration factor calculation formula, and wherein $$Fcts = 2TSWt \sin \theta / \alpha \qquad (a)$$

$$Ftss = TSWt/\alpha \qquad (b);$$

storing the fracture strength parameter by each steel type in a parameter storage arrangement; and analyzing a fracture of the spot welded portion by providing the fracture strength parameter stored in the parameter storage arrangement into a fracture prediction formula in which a deformation at a periphery of the spot welding portion is modeled by a finite element procedure, wherein the fracture prediction formula is based on a shear force and a vertical force with respect to the spot welded portion.

9. The fracture prediction method of claim 8, wherein the shear force is provided in a direction along a member surface of an element that connects members with each other in which the spot welding is modeled, and the vertical force is provided in a direction that connects members with each other orthogonally to the shear force.

10. The fracture prediction method of claim 8, wherein the shear force is determined one after another during a deformation of a collision analysis reproduced using the finite element procedure.

11. A fracture prediction method for a spot welded portion, comprising:

inputting at least one of a tensile strength (TS) a material, a plate thickness t, a nugget diameter d of a spot welding, a plate width w of a particular joint, or a rotation angle $\theta$ of the particular joint in a tension test which is at least one of a cross tension testing procedure or a shear tension testing procedure at a spot welded joint;

determining a fracture limit load (Fcts) as a fracture strength parameter of the spot welded portion in a cross tension using a formula (a) and a fracture limit load (Ftss) as a fracture strength parameter of the spot welded portion in a shear tension using a formula (b), based on a stress concentration factor $\alpha$ and at least one of the inputted tensile strength TS of the material, the plate thickness t, the nugget diameter d of the spot welding, the plate width w of the joint, or the rotation angle $\theta$ of the joint in the tension testing procedure, wherein the stress concentration factor $\alpha$ is at least one of (i) defined by a formula of (TS) / (mean tensile stress $\sigma o$) or (ii) calculated using a stress concentration factor calculation formula, and wherein $$Fcts = 2TSWt \sin \theta / \alpha \qquad (a)$$

$$Ftss = TSWt/\alpha \qquad (b);$$

storing the fracture strength parameter by each steel type in a parameter storage arrangement; and analyzing a fracture of the spot welded portion by providing the fracture strength parameter stored in the parameter storage arrangement into a fracture limit line in which a deformation at a periphery of the spot welding portion is modeled by a finite element procedure, wherein the fracture limit line is created as a curve based on a shear force and a vertical force with respect to the spot welded portion.

12. The fracture prediction method of claim 11, wherein the shear force is provided in a direction along a member surface of an element that connects members with each other in which the spot welding is modeled, and the vertical force is provided in a direction that connects members with each other orthogonally to the shear force.

13. The fracture prediction method of claim 11, wherein the shear force is determined one after another during a deformation of a collision analysis reproduced using the finite element procedure.

14. The fracture prediction method of claim 11, wherein the fracture strength curve provides a graphic representation written by measuring the fracture strength parameter by a test in which at least one of the material strength, the plate thickness, the nugget diameter of the spot welding, the plate width of the joint, or the rotation angle of the particular joint in the tension testing procedure are varied.

15. A non-transitory computer storage arrangement provided for a fracture prediction of a spot welded portion to design a circuit, comprising:

a first set of instructions which, when executed by a processing arrangement, configure the processing arrangement to determine a fracture limit load (Fcts) as a fracture strength parameter of the spot welded portion in a cross tension using a formula (a), and a fracture limit load (Ftss) as a fracture strength parameter of the spot welded portion in a shear tension using a formula (b), based on a stress concentration factor α and at least one of a tensile strength (TS) of a material, a plate thickness t, a nugget diameter d of a spot welding, a plate width w of a particular joint, and a rotation angle θ of the particular joint in a tension testing procedure based on at least one of a cross tension testing procedure or a shear tension testing procedure at a spot welded joint, wherein the stress concentration factor α is at least one of (i) defined by a formula of (TS)/(mean tensile stress σo) or (ii) calculated using a stress concentration factor calculation formula, and wherein $$Fcts = 2TSWt \sin\theta/\alpha \quad (a)$$

$$Ftss = TSWt/\alpha \quad (b);$$

a second set of instructions which, when executed by the processing arrangement, configure the processing arrangement to store the fracture strength parameter by each steel type in a parameter storage arrangement; and a third set of instructions which, when executed by the processing arrangement, configure the processing arrangement to analyze a fracture of the spot welded portion by providing the fracture strength parameter stored in the parameter storage arrangement into a fracture prediction formula in which a deformation at a periphery of the spot welding portion is modeled by a finite element procedure, wherein the fracture prediction formula is based on a shear force and a vertical force with respect to the spot welded portion.

16. The computer storage arrangement of claim 15, wherein the shear force is provided in a direction along a member surface of an element that connects members with each other in which the spot welding is modeled, and the vertical force is provided in a direction that connects members with each other orthogonally to the shear force.

17. The computer storage arrangement of claim 13, wherein the shear force is determined by the processing arrangement one after another during a deformation of a collision analysis reproduced using the finite element procedure.

18. A non-transitory computer storage arrangement provided for a fracture prediction of a spot welded portion to design a circuit, comprising:

a first set of instructions which, when executed by a processing arrangement, configure the processing arrangement to determine a fracture limit load (Fcts) as a fracture strength parameter of the spot welded portion in a cross tension using a formula (a) and a fracture limit load (Ftss) as a fracture strength parameter of the spot welded portion in a shear tension using a formula (b), based on a stress concentration factor α and at least one of a tensile strength (TS) of a material, a plate thickness t, a nugget diameter d of a spot welding, a plate width w of a particular joint, and a rotation angle θ of the particular joint in a tension testing procedure based on at least one of a cross tension testing procedure or a shear tension testing procedure at a spot welded joint, wherein the stress concentration factor α is at least one of (i) defined by a formula of (TS) / (mean tensile stress σo) or (ii) calculated using a stress concentration factor calculation formula, and wherein $$Fcts = 2TSWt \sin\theta/\alpha \quad (a)$$

$$Ftss = TSWt/\alpha \quad (b);$$

a second set of instructions which, when executed by the processing arrangement, configure the processing arrangement to store the fracture strength parameter by each steel type in a parameter storage arrangement; and a third set of instructions which, when executed by the processing arrangement, configure the processing arrangement to analyze a fracture of the spot welded portion by providing the fracture strength parameter stored in the parameter storage arrangement into a fracture limit line in which a deformation at a periphery of the spot welding portion is modeled by a finite element procedure, wherein the fracture limit line is created as a curve based on a shear force and a vertical force with respect to the spot welded portion.

19. The computer storage arrangement of claim 18, wherein the shear force is provided in a direction along a member surface of an element that connects members with each other in which the spot welding is modeled, and the vertical force is provided in a direction that connects members with each other orthogonally to the shear force.

20. The computer storage arrangement of claim 18, wherein the shear force is determined by the processing arrangement one after another during a deformation of a collision analysis reproduced using the finite element procedure.

21. The computer storage arrangement of claim 18, wherein the fracture strength curve provides a graphic representation written by measuring the fracture strength parameter by a test in which at least one of the material strength, the plate thickness, the nugget diameter of the spot welding, the plate width of the joint, or the rotation angle of the particular joint in the tension testing procedure are varied.

22. A non-transitory computer-accessible medium including a computer program thereon which, when executed by a processing arrangement, configures the processing arrangement to perform the procedures comprising:

determining a fracture limit load (Fcts) as a fracture strength parameter of a spot welded portion in a cross tension using a formula (a), and a fracture limit load (Ftss) as a fracture strength parameter of the spot welded portion in a shear tension using a formula (b), based on a stress concentration factor α and at least one of a tensile strength (TS) of a material, a plate thickness t, a nugget diameter d of a spot welding, a plate width w of a joint, and a rotation angle θ of the joint in a tension testing procedure obtained based on at least one of a cross tension testing procedure or a shear tension testing procedure at a spot welded joint, wherein the stress concentration factor α is at least one of (i) defined by a formula of ( TS)/(mean tensile stress σo) or (ii) calculated using a stress concentration factor calculation formula, and wherein $$Fcts = 2TSWt \sin\theta/\alpha \quad (a)$$

$$Ftss = TSWt/\alpha \quad (b);$$

storing the fracture strength parameter by each steel type in a parameter storage arrangement; and analyzing a fracture of the spot welded portion by providing the fracture strength parameter stored in the parameter storage arrangement into a fracture prediction formula in which a deformation at a periphery of the spot welding portion is modeled by a finite element procedure, wherein the fracture prediction formula is based on a shear force and a vertical force with respect to the spot welded portion.

23. The computer-accessible medium of claim 22, wherein the shear force is provided in a direction along a member surface of an element that connects members with each other in which the spot welding is modeled, and the vertical force is provided in a direction that connects members with each other orthogonally to the shear force.

24. The computer-accessible medium of claim 22, wherein the shear force is determined by the processing arrangement one after another during a deformation of a collision analysis reproduced using the finite element procedure.

25. A non-transitory computer-accessible medium including a computer program thereon which, when executed by a processing arrangement, configures the processing arrangement to perform the procedures comprising:

determining a fracture limit load (Fcts) as a fracture strength parameter of a spot welded portion in a cross tension using a formula (a) and a fracture limit load (Ftss) as a fracture strength parameter of the spot welded portion in a shear tension using a formula (b), based on a stress concentration factor $\alpha$ and least one of a tensile strength (TS) of a material, a plate thickness t, a nugget diameter d of a spot welding, a plate width w of a joint, and a rotation angle $\theta$ of the joint in a tension testing procedure obtained based on a cross tension testing procedure or a shear tension testing procedure at a spot welded joint, wherein the stress concentration factor $\alpha$ is at least one of (i) defined by a formula of (TS) / (mean tensile stress $\sigma o$) or (ii) calculated using a stress concentration factor calculation formula, and wherein $$Fcts = 2TSWt \sin \theta / \alpha \qquad (a)$$

$$Ftss = TSWt / \alpha \qquad (b);$$

storing the fracture strength parameter by each steel type in a parameter storage arrangement; and analyzing a fracture of the spot welded portion by installing the fracture strength parameter stored in the parameter storage arrangement into a fracture limit line in which a deformation at a periphery of the spot welding portion is modeled by a finite element procedure, wherein the fracture limit line is created as a curve based on a shear force and a vertical force with respect to the spot welded portion.

26. The computer-accessible medium of claim 25, wherein the shear force is provided in a direction along a member surface of an element that connects members with each other in which the spot welding is modeled, and the vertical force is provided in a direction that connects members with each other orthogonally to the shear force.

27. The computer-accessible medium of claim 25, wherein the shear force is determined by the processing arrangement one after another during a deformation of a collision analysis reproduced using the finite element procedure.

28. The computer-accessible medium of claim 25, wherein the fracture strength curve provides a graphic representation written by measuring the fracture strength parameter by a test in which at least one of the material strength, the plate thickness, the nugget diameter of the spot welding, the plate width of the joint, or the rotation angle of the particular joint in the tension testing procedure are varied.

* * * * *